United States Patent [19]

Fujii et al.

[11] 4,122,258

[45] Oct. 24, 1978

[54] PROCESS FOR PRODUCING DESACETOXYCEPHALOSPORIN DERIVATIVES BY HEATING A PENICILLIN-1-OXIDE IN PRESENCE OF AN ORGANIC SULFIDE

[75] Inventors: Shoichiro Fujii, Kyoto; Michiyuki Sendai, Osaka; Kenzo Naito, Kyoto; Masayasu Kato, Ashiya, all of Japan

[73] Assignee: Takeda Chemical Industries, Ltd., Osaka, Japan

[21] Appl. No.: 340,892

[22] Filed: Mar. 13, 1973

[30] Foreign Application Priority Data

Mar. 23, 1972 [JP] Japan .................................. 47-29459

[51] Int. Cl.$^2$ ........................................... C07D 501/10
[52] U.S. Cl. ..................................................... 544/18
[58] Field of Search ...................... 260/243 C; 544/18

[56] References Cited

U.S. PATENT DOCUMENTS

| | | | |
|---|---|---|---|
| 3,632,850 | 1/1972 | Garbrecht | 260/243 C |
| 3,725,397 | 4/1973 | Graham et al. | 260/243 C |
| 3,725,399 | 4/1973 | Ellerton et al. | 260/243 C |
| 3,843,637 | 10/1974 | Rubinfeld et al. | 260/243 C |
| 3,852,281 | 12/1974 | Verweij | 260/243 C |
| 3,852,295 | 12/1974 | Graham et al. | 260/243 C |
| 3,862,181 | 1/1975 | Davis et al. | 260/243 C |
| 3,890,314 | 6/1975 | Ishimaru et al. | 260/243 C |
| 3,959,266 | 5/1976 | Dallasta | 544/18 |

Primary Examiner—Donald G. Daus
Assistant Examiner—Mark L. Berch
Attorney, Agent, or Firm—Wenderoth, Lind & Ponack

[57] ABSTRACT

Penicillin-1-oxides are rearranged into the corresponding 3-desacetosycephalosporin derivatives in an inert organic solvent in the concomitant presence of an acid catalyst and an organic sulfide in a good yield and with a high purity.

35 Claims, No Drawings

PROCESS FOR PRODUCING DESACETOXYCEPHALOSPORIN DERIVATIVES BY HEATING A PENICILLIN-1-OXIDE IN PRESENCE OF AN ORGANIC SULFIDE

This invention relates to an improved method for converting penicillin-1-oxides to 3-desacetoxycephalosporin derivatives.

It was found by R. B. Morin et al. (J.A.C.S. 85,1896(1963)) that penicillin-1-oxides were rearranged into the corresponding 3-desacetoxycephalosporin derivatives in the presence of p-toluenesulfonic acid. This discovery was followed by many improvement proposals in connection with such parameters as catalysts, solvents and reaction conditions. Particularly in respect of catalysts, a number of phosphoric acid and sulfonic acid derivatives have been tried. However, so long as these acid catalysts are employed singly, the reaction yields attainable are low and the proportion of byproducts is high in both variety and quantity. Thus, the isolation and purification of product compounds, for instance, is accompanied by much difficulty.

Recently, it was reported that this type of rearrangement to 3-desacetoxycephalosporin derivatives was conducted in the presence of salts or complexes of nitrogenous bases with a pKb value not smaller than 4 and acids in inert organic solvents to give the objective compounds in the yield of 37.7-76.5%(Chemical Abstracts 74 13172 k, German Offenlegungsschrift 2011376). The presence of the base, however, promotes the degradation of the starting and objective compounds as well as the rearrangement reaction and therefore, many kinds of the degradation products and byproducts inclusive of colored impurities accompany by this method.

The extensive study undertaken by the present inventors to overcome these difficulties led them to the finding that the yield of the rearrangement reaction can be significantly enhanced by conducting the reaction in the concomitant presence of acid catalysts and organic sulfides. The process according to this invention offers a number of advantages. Namely, the yield of the rearrangement reaction is increased; the procedure is facilitated; the formation of byproducts, rupture of the lactam ring, coloring of the product, the formation of peroxides, degradation of the starting and objective compounds, unstableness of the reaction and other undesirable phenomena are considerably suppressed; the isolation of the pure product compound is so easy that no troublesome after-treatment is required, and so on.

The penicillin-1-oxides which are to be employed in the reaction of this invention can be prepared by the per se conventional oxidation of penicillins which are available at low cost from fermentation processes, such as penicillin G and penicillin V, or of semi-synthetic penicillins which can be easily synthesized from 6-aminopenicillanic acid. Further, the above-mentioned oxides can be advantageously prepared by the oxidation of such material compounds with urea-hydrogen, peroxide.

Thus, these penicillin-oxides may be represented by the general formula:

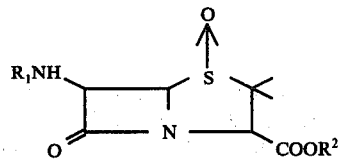

(wherein $R_1$ is a protective group for the amino group such as silyl or an acyl group; and $R_2$ is a hydrogen or a protective group for the carboxyl group such as an ester residue).

In the formula (1), the acyl group may be any suitable acyl group such as phenylacetyl, phenoxyacetyl, phenylglycyl, thienylacetyl, α-carboxyphenylacetyl, cyclohexenylglycyl, β-methylsulfonylethoxycarbonyl or α-sulfophenylacetyl or the like. Other protective groups may be exemplified by silyl group (e.g. trimethylsilyl, triphenylsilyl, trimethoxysilyl, triethoxysilyl, etc.), silenyl group (e.g. dimethylsilenyl, diethylsilenyl, dimethoxysilenyl, diethoxysilenyl, etc.), triphenylmethyl, etc. The ester residue $R^2$ is exemplified by such common groups as methyl, ethyl, trimethylsilyl, dimethylsilyl, methoxymethyl, ethoxymethyl, methylmercaptomethyl, β-methylsulfonylethyl, trichloroethyl, benzyl, nitrophenyl, benzhydryl, phenacyl, trityl, phenyl, etc., and the residues which can be easily removed by hydrolysis or alcoholysis are generally preferred. Of course, the ester residue need not be removed when the ester itself is pharmacologically active. Also, when the side-chain acyl groups of penicillin-1-oxides contain amino, carboxyl, sulfo or/and hydroxyl groups, for instance, there are cases in which these reactive groups in the side chain are desirably protected by a procedure which is conventional per se.

The rearrangement reaction of this invention is conducted in the presence of acid catalysts. The acid catalysts may be selected generally from per se known catalyst which accelerate the rearrangement reaction. The acid catalyst thus used is exemplified by phosphoric acid and its derivatives such as orthophosphoric acid, polyphosphoric acid, pyrophosphoric acid, methanephosphonic acid, ethanephosphonic acid, trichloromethanephosphonic acid, iodomethanephosphonic acid, benzenephosphonic acid, bromobenzenephosphonic acid, nitrobenzenephosphonic acid, β-iodoethyl phosphate, β-bromoethyl phosphate, β-methoxyethyl phosphate, β,β,β-trichloroethyl phosphate, 2-chloroethyl phosphate, benzyl phosphate, p-tolyl phosphate, methyl phosphate, ethyl phosphate, phenyl phosphate, 1-naphthyl phosphate, 2-naphthyl phosphate, and so forth; sulfuric acid derivatives such as 10-D-camphorsulfonic acid, methanesulfonic acid, p-toluenesulfonic acid, etc.; composite metal oxides such as silica-alumina, silica-boria, silica-magnesia, silica-zirconia, alumina-boria, thoria-silica, thoria-alumina, silica-alumina-zirconia, silica-alumina-magnesia, silica-alumina-thoria, synthetic zeolites, natural zeolite, acid clay, kaolin, bentonite, etc.; complexes of compounds (oxides, hydroxides, carbonates and organic acid salts of Group II or III metals, such as magnesium, calcium, barium, aluminum, etc., with phosphoric acid or sulfuric acid derivatives; silica-phosphoric acid; and so forth.

In conducting the reaction of this invention, such acid catalysts are used in combination with organic sulfides. The molecular weight of the sulfides is preferably up to 500, desirably 220 and the sulfur atom of the organic sulfides has lone electron pairs and does not receive steric hindrance. Of course, the organic sulfides should not have other functional group detrimental to the desired rearrangement reaction. Thus, dialkyl sulfides such as diethyl sulfide, ethyl n-propyl sulfide, ethyl isopropyl sulfide, 1,2-di(methylmercapto)ethane, 1,2-dimercaptoethane, di-n-propyl sulfide, di-n-butyl sulfide, n-butyl ethyl sulfide, dodecyl methyl sulfide, 1,2-di(n-dodecylmercapto)ethane, etc.; cyclic sulfides such as tetra-methylene sulfide, pentamethylene sulfide, 1,4-dithiane, s-trithiane, etc.; aromatic sulfides such as phenyl methyl sulfide, 2thienylethyl sulfide, diphenyl sulfide, dibenzyl sulfide, etc.; hydroxy or alkoxy sulfides such as 62 -hydroxyethylmethyl slfide, $\gamma$-hydroxypropylethyl sulfide, $\beta$-hydroxyethylphenyl sulfide, thiodiglycol, $\gamma,\gamma'$-dihydroxypropyl sulfide, 1,2-di-(2-hydroxyethylthio)ethane, $\delta$-hydroxypentylethyl sulfide, 2-hydroxypropylethyl sulfide, $\beta,\beta'$-diethoxyethyl sulfide, ethylethoxymethyl sulfide, etc.; ketones, esters and cyanosulfides such as $\beta$-ethylmercaptoethyl methyl ketone, dimethyl thiodiglycollate, diethyl thiodiglycollate, 2,2'-dicyanoethyl sulfide, etc.; and other sulfide compounds such as sulfur-containing polymers, e.g. polypropylene sulfide may be generally employed. While the rearrangement reaction may be carried out in the presence of a large excess of the sulfides, the sulfides are preferably used in amounts ranging from 2 to 10 times of the amount of, say, the phosphoric acid catalyst.

It is also possible to employ a compound of a structure such that an organic sulfide has been attached to an acid, e.g. sulfide phosphoric acid esters such as $\beta$-methylsulfinylpropyl phosphate, etc. These sulfides can be easily removed from the reaction mixture after completion of ring enlargement by such procedures as washing with water, filtration, distillation and recrystallization. Besides, the sulfides may be reused by distillation with the solvents used.

The effective amount of the catalyst generally varies somewhat with different penicillin-1-oxides. Generally, however, the phosphoric acid catalyst, for instance, is used in an amount corresponding to one-half or less and, preferably, one-twentieth to three-tenth of the amount of the penicillin-1-oxide. The inert solvent to be employed is exemplified by amides(e.g. dimethylformamide, dimethylacetamide, etc.), carbamates (e.g. methyl N,N-dimethylcarbamate, ethyl N,N-dimethylcarbamate, etc.), dioxane, ketones (e.g. methyl isobutylketone, etc.), esters (e.g. isobutyl acetate, n-butyl acetate, isopropyl acetate, etc.), hydrocarbons (e.g. benzene, toluene, xylene, etc.), alcohols (e.g. isopropanol, tert.-butanol, sec.-butanol, tert.-amyl alcohol, sec.-amyl alcohol, 3-pentanol, 3-methyl-2-butanol, neopentyl alcohol, 4-methyl-2-pentanol, etc.), ethers (e.g. diethylene glycol dimethyl ether, diethoxyethylene glycol, methyl n-amyl ether, ethyl tert.-amyl ether, n-propyl isobutyl ether, isopropyl n-butyl ether, tert.-butyl n-propyl ether, ethyl n-amyl ether, ethyl etc.), halogenated hydrocarbons (e.g. amyl chloride, 1,1,2-trichloroethane, 1,1,1,2-tetrachloroethane, 1,1,2,2-tetrachloroethane, 1,2-dichloropropane, chlorobenzene, etc.), sulfolane, hexamethylphosphoric triamide, etc. as well as mixtures of such solvents.

While the reaction may generally be conducted in the temperature range of 80° to 150° C., it is usually preferable to conduct the reaction at 95° to 125° C. The reaction is preferably carried out until a maximal yield is attained, that is to say, generally for 1 to 20 hours. The reaction may be conducted in currents of an inert gas such as nitrogen gas but the employment of the sulfides in the present process eliminates the need of such conditions in many cases. When the solvent is refluxed, the reaction yield can be further enhanced by interposing a dehydrating agent (e.g. molecular sieve, barium oxide, calcium oxides, etc.) in the return pass of the reflux circuit so that the water byproduced in the course of the reaction will be removed from the reaction system. The dehydration can also be realized by azeotropic distillation of the solvents and water.

The 3-deacetoxycephalosporin derivatives which can be produced in the foregoing manner may be illustrated e.g. by the general formula:

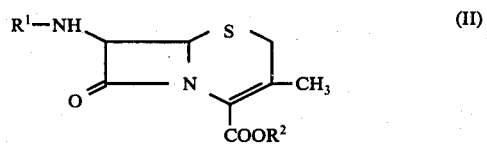

(II)

wherein $R^1$ and $R^2$ have the same meaning as above. These derivatives (II) are antibiotics of considerable importance and may if desired be converted to still more potent cephalosporins by such procedures as interacylation, deacylation and subsequent acylation, deesterification and so forth.

It is to be understood that the following examples are solely for the purpose of illustration and not to be construed as limitations of this invention, and that many variations may be resorted to without departing from the spirit and scope of this invention. In this specification, "g.", "ml.", "cm", "mm.", "IR", "NMR", "TLC" and "UV" are "gram", "milliliter", "centimeter", "millimeter", "millimicron", "Infrared spectrum", "Nuclear magnetic resonance", "Thin layer chromatography" and "Ultraviolet spectrum", respectively. Temperatures are all uncorrected, and percentages are all on the weight basis. The yield in each example is calculated as that of pure product. That is to say, the yield is calculated by multiplying the crude yield with the purity of the product which is found both by the following TLC-UV method and liquid chromatography.

TLC-UV METHOD

A solution of a product is spotted on a TLC plate (Kiesel gel GF 254, sold by E. Merck in Germany under this trade name, 0.25 mm. thickness, 20×20cm.) and developed with a mixture of benzene, acetone and acetic acid (40:15:2). After air-dried, the spots of the objective compound are gathered and subjected to extraction with a 50% aqueous ethanol using centrifugal separator. The purity is estimated from the UV absorption of the supernatant at 260m$\mu$. using a linear relationship (calibration curve) between the spotted quality and the absorbance of a pure compound.

LIQUID CHROMATOGRAPHY

Using liquid chromatograph (ALC-202, made by Waters Associates Co., column: stainless, ⅛ inch in diameter, 2 meter in length, packing: Corasil Type II (sold by Waters Associates Co. under this trade name), the sample is eluted at the conditions of column temperature 25° C. and pressure: 300 pound per square inch with a mixture of ethanol 4 ml. acetic acid 2 ml. and supernatant 100 ml. of a mixture of n-hexane, isopropyl ether, ethanol and water (3:20:5:4). The purity is esti-

EXAMPLE 1

In 100 ml. of dry dioxane are dissolved 0.40 g. of diethyl sulfide and 0.12 g. of orthophosphoric acid. Then, 4.56 g. of penicillin G sulfoxide β-methylsulfonylethyl ester is added, with stirring. The mixture is heated under reflux in currents of nitrogen gas for 15 hours. After the reaction has gone to completion, 0.4 g. of calcium carbonate is added, followed by vigorous stirring, The mixture is filtered with the aid of a filter aid (Hyflo Super-cel sold by Johns-Manvilles Co. in USA under this trade name) and the filtrate is concentrated under reduced pressure to harvest crystals. These crystals are taken to a glass filter and washed well with water, followed by drying. Recrystallization from acetone-petroleum ether yields 3.30 g. of 7-phenylacetamido-3-desacetoxycephalosporanic acid β-methylsulfonylethyl ester (yield 75.3%). m.p.157°–159° C.

IR(KBr): 3300, 1775, 1725, 1655, 1535cm$^{-1}$.

NMR(CDCl$_3$): 2.16(3H), 2.90(3H), 3.33(2H), 3.40(2H), 3.60(2H), 4.65(2H), 4.94(1H), 5.66(1H), 6.70(1H), 7.16(5H)ppm.

TLC: a single spot.

Incidentally, penicillin G sulfoxide β-methylsulfonylethyl ester can be prepared by, for example, the following procedure.

In 100 ml. of dry methylene chloride is suspended 3.50 g. of penicillin G sulfoxide and at a temperature of not more than 10° C., 8.54 g. of pyridine is added. Then, a solution of 20.2 g. β-methylsulfonylethyl chloroformate in 30 ml. of dry methylene chloride is added dropwise at 0°–5° C.

After the dropwise addition has been completd, the mixture is allowed to react at 0°–5° C. for 30 minutes. Then, 80 ml. of water and 100 ml. of methylene chloride are added.

After stirring well, the mixture is allowed to separate into layers, the methylene chloride layer being taken. The methylene chloride solution is washed with 5% HCl, water, 5% aqueous sodium hydrogen carbonate solution and water (two 50 ml. portions each) in the order mentioned. After drying, the methylene chloride is distilled off under reduced pressure and the residue is recrystallized from methanol. The procedure yields penicillin G sulfoxide β-methylsulfonylethyl ester. m.p.137°–138° C.

IR(KBr): 1783, 1765, 1690cm$^{-1}$.

NMR(CDCl$_3$)δ: 1.22(3H), 1.70(3H), 2.98(3H), 3.39(2H), 3.58(2H), 4.62(3H), 5.00(1H), 6.02(1H), 7.30(5H)ppm.

EXAMPLE 2

In 100 ml. of dioxane containing 0.45 g. of isopropyl ethyl sulfide and 0.1 g. of orthophosphoric acid, there is dissolved 4.56 g. of penicillin G sulfoxide β-methylsulfonylethyl ester. The solution is refluxed. The condensed vapor is guided through a cylinder of filter paper with barium oxide before it is returned to the reactor to remove the water. The reaction system is held under reflux in nitrogen gas streams for 15 hours. The reaction mixture thus obtained is cooled and the dioxane and isopropylethyl sulfide are distilled off under reduced pressure. The residue is dissolved in 100 ml. of methylene chloride and the solution is washed with 1% aqueous sodium hydrogen carbonate and aqueous sodium chloride (50 ml. each) in that order. The solution is dried and the methylene chloride is distilled off under reduced pressure, whereupon yellowish brown crystals are obtained. Recrystallization from acetone-petroleum ether yields 3.52 g. (80.4%) of 7-phenylacetamido-3-desacetoxycephalosporanic acid β-methylsulfonylethyl ester.

EXAMPLE 3

In 90 ml. of dioxane containing 0.86 g. dibenzyl sulfide and 0.14 g. orthophosphoric acid, there is dissolved 4.56 g. of penicillin G sulfoxide β-methylsulfonylethyl ester.

In the same manner as Example 2, the reaction mixture is refluxed in nitrogen streams for 12 hours while the water is removed. After the reaction has been completed, the mixture is treated in the same manner to obtain 3.02g. (69%) of 7-phenylacetamido-3-desacetoxycephalosporanic acid β-methylsulfonylethyl ester.

EXAMPLE 4

In 80 ml. of a mixture of sec.-butanol and toluene (3:1) containing 0.50 g. of 1,4-dithiane and 0.15 g. of orthophosphoric acid, there is dissolved 4.72 g. of penicillin V sulfoxide β-methylsulfonylethyl ester and the mixture is refluxed in nitrogen streams for 18 hours while the water is removed by a procedure similar to that described in Example 2(internal temperature 99° C.). After the reaction has been completed, the solvent is distilled off under reduced pressure, whereupon a yellow-brown solid residue is obtained. This solid washed well with water, dried and recrystallized from acetone-n-hexane. The procedure yields 3.27 g. of 7-phenoxyacetamido-3-desacetoxycephalosporanic acid β-methylsulfonylethyl ester (72.0%).

m.p.158°–160° C.

IR(KBr): 3350, 1775, 1730, 1700, 1530cm$^{-1}$.

NMR(d$_6$—DMSO) δ: 2.15(3H), 3.00(3H), 3.46(4H), 4.63(4H), 5.10(1H), 6.8–7.4(5H) ppm.

TLC: a single spot.

EXAMPLE 5

In 60 ml. of methyl N,N'-dimethylcarbamate ester containing 0.50 g. of s-trithiane and 0.15 g. of orthophosphoric acid, there is dissolved 4.56 g. of penicillin G sulfoxide β-methylsulfonylethyl ester and the solution is allowed to react in nitrogen streams at 110° to 115° C. for 8 hours. After the reaction has been completed, the solvent is distilled off under reduced pressure and the residue is treated in the same manner as Example 2. The procedure yields 2.81 g. (64.2%) of 7-phenylacetamido-3-desacetoxycephalosporanic acid β-methylsulfonylethyl ester.

EXAMPLE 6

In 100 ml. of dioxane is dissolved 1.00 g. of a 3:1 (mole ratio) mixture of β-methylmercaptoethanol and orthophosporic acid. With stirring, 4.56 g. of penicillin G sulfoxide β-methylsulfonylethyl ester is added and the mixture is reacted and treated in the same manner as Example 2. The procedure yields 3.38 g. (77.2%) of 7-phenylacetamido-3-desacetoxycephalosporanic acid β-methylsulfonylethyl ester.

EXAMPLE 7

In 60 ml. of methyl N,N'-dimethylcarbamate is dissolved 1.00 g. of a 4:1 (mole ratio) mixture of β-methylmercaptoethanol and orthophosphoric cid. Under stirring, 4.56 g. of penicillin G sulfoxide β-methylsulfonylethyl ester is added and the mixture is reacted in nitrogen streams at 110°–115° C. for 3 hours. After the reaction has been completed, the reaction mixture is treated by a procedure similar to that described in Example 5, whereupon 3.11 g. (71.0%) of 7-phenylacetamido-3-desacetoxycephalosporanic acid β-methylsulfonylethyl ester is obtained.

EXAMPLE 8

In 80 ml. of a mixture (7:3) of sec.-amyl alcohol and toluene containing 0.72 g. of γ-hydroxypropyl ethyl sulfide and 0.46 g. of trichloroethyl phosphate, there is dissolved 4.72 g. of penicillin V sulfoxide β-methylsulfonylethyl ester and the resulting mixture is refluxed in nitrogen gas streams for 10 hours while the water is removed in the same manner as Example 2 (internal temperature 106° C.). After the reaction has been completed, the reaction mixture is treated by a procedure similar to that described in Example 4. The procedure yields 3.20 g. (69.8%) of 7-phenoxyacetamido-3-desacetoxycephalosporanic acid β-methylsulfonylethyl ester.

EXAMPLE 9

In 200 ml. of dioxane is dissolved 2.0 g. of a mixture (4:1, mole ratio) of thiodiglycol and orthophosphoric acid. Under stirring, 9.12 g. of penicillin G sulfoxide β-methylsulfonylethyl ester and the mixture is reacted and treated in the same manner as Example 2. The procedure yields 7.19 g. (82.1%) of 7-phenylacetamido-3-desacetoxycephalosporanic acid β-methylsulfonylethyl ester.

EXAMPLE 10

In 200 ml. of dioxane is dissolved 2.0 g. of a mixture (5:1, mole ratio) of thiodiglycol and orthophosphoric acid, followed by the addition of 9.12 g. of penicillin G sulfoxide β-methylsulfonylethyl ester. The mixture is reacted and after-treated in the same manner as Example 2. The procedure yields 6.98 g. (79.8%) of 7-phenylacetamido-3-desacetoxycephalosporanic acid β-methylsulfonylethyl ester.

EXAMPLE 11

A mixture comprising 2.32 g. of a 6:1 mixture of thiodiglycol and orthophosphoric acid, 9.12 g. of penicillin G sulfoxide β-methylsulfonylethyl ester and 200 ml. of dioxane is reacted for 14 hours and the reaction product is after-treated in the same manner as Example 2. The procedure yields 7.05 g. (80.5%) of 7-phenylacetamido-3-desacetoxycephalosporanic acid β-methylsulfonylethyl ester.

EXAMPLE 12

A mixture comprising 9.12 g. of penicillin G sulfoxide β-methylsulfonylethyl ester, 1.46 g. of thiodiglycol, 0.72 g. of trichloroethyl phosphate and 200 ml. of dioxane is reacted for 15 hours and the reaction product is after-treated in the same manner as Example 2. The procedure yields 6.88 g. (78.6%) of 7-phenylacetamido-3-desacetoxycephalosporanic acid β-methylsulfonylethyl ester.

EXAMPLE 13

In 200 ml. of diethylene glycol dimethyl ether (diglyme) is dissolved 2.0 g. of a 4:1 mixture of thiodiglycol and orthophosphoric acid, followed by the addition of 9.12 g. of penicillin G sulfoxide β-methylsulfonylethyl ester. The mixture is reacted at 110°–115° C. for 8 hours and the reaction product is after-treated in the same manner as Example 2. The procedure yields 6.04 g. (69.9%) of 7-phenylacetamido-3-desacetoxycephalosporanic acid β-methylsulfonylethyl ester.

EXAMPLE 14

In 180 ml. of dioxane containing 1.34 g. of 1,2-di-(2'-hydroxyethylthio)ethane and 0.31 g. of orthophosphoric acid, there is dissolved 9.12 g. of penicillin G sulfoxide β-methylsulfonylethyl ester and the mixture is refluxed.

The reaction is carried out in nitrogen streams for 15 hours while the water is removed in the same manner as Example 2. After the reaction has been completed, the dioxane is distilled off under reduced pressure and the residue is dissolved in 400 ml. of methylene chloride. The solution is washed with 1% aqueous sodium hydrogen carbonate and, then, with aqueous sodium chloride. After the methylene chloride solution is dried, the solvent is distilled off under reduced pressure to harvest yellowish white crystals, The crystals are recrystallized from acetone-petroleum ether. The mother fluid is concentrated and column-chromatographed on silica gel to isolate the cephem compound. The procedure yields 7.41 g. (84.6%) of 7-phenylacetamido-3-desacetoxycephalosporanic acid β-methylsulfonylethyl ester.

EXAMPLE 15

A mixture of 9.12 g. of penicillin G sulfoxide β-methylsulfonylethyl ester, 0.72 g. of 1,2-di(2'-hydroxyethylthio)ethane, 0.16 g. of orthophosphoric acid and 80 ml. of dioxane is reacted and after-treated in the same manner as Example 14. The procedure yields 7.48 g. (85.4%) of 7-phenylacetamido-3-desacetoxycephalosporanic acid β-methylsulfonylethyl ester.

EXAMPLE 16

In 100 ml. of ethylene glycol diethyl ether containing 0.72 g. of 1,2-di(2'-hydroxyethylthio)ethane and 0.15 g. of orthophosphoric acid, there is dissolved 3.80 g. of penicillin V sulfoxide methyl ester, and the resulting solution is reacted in nitrogen streams at 110°–115° C. for 8 hours. After the reaction has been completed, the reaction mixture is after-treated by a procedure similar to that described in Example 2 and recrystallized from methanol. The procedure yields 2.68 g. (74.1%) of 7-phenoxyacetamido-3-desacetoxycephalosporanic acid methyl ester. m.p.141°–142° C.

IR(KBr): 1775, 1725, 1670cm$^{-1}$.

NMR(CDCl$_3$)δ: 2.14(3H), 3.15(1H, 18Hz), 3.55(1H, 18Hz), 3.83(3H), 4.58(2H), 5.00(1H, 4.8Hz), 5.84(1H, 4.8 and 9.2 Hz), 6.84–7.55(6H) ppm.

EXAMPLE 17

In 80 ml. of a 7:3 mixture of sec.-amyl alcohol and toluene containing 0.72 g. of 1,2-di(2'-hydroxyethylthio)ethane and 0.15 g. of orthophosphoric acid, there is dissolved 4.56 g. of penicillin G sulfoxide β-methylsulfonylethyl ester and the resulting solution is reacted for 10 hours and after-treated in the same manner as Example 8. The procedure yields 3.13 g. (71.4%) of 7-phenylacetamido-3-desacetoxycephalosporanic acid β-methylsulfonylethyl ester.

EXAMPLE 18

In 50 ml. of dioxane containing 0.37 g. of thioanisol and 0.10 g. of orthophosphoric acid, there is dissolved 3.80 g. of penicillin V sulfoxide methyl ester. The resulting solution is reacted and after-treated in the same manner as Example 2. The procedure yields 2.48 g. (68.5%) of 7-phenoxyacetamido-3-desacetoxycephalosporanic acid methyl ester.

EXAMPLE 19

In 50 ml. of dioxane containing 0.37 g. of 1,2-di(methylmercapto)ethane and 0.10 g. of orthophosphoric acid, there is dissolved 3.80 g. of penicillin V sulfoxide methyl ester. The resulting solution is reacted and after-treated in the same manner as Example 2. The procedure yields 3.08 g. (85.1%) of 7-phenoxyacetamido-3-desacetoxycephalosporanic acid methyl ester.

EXAMPLE 20

In 50 ml. of dioxane containing 0.54 g. of dimethyl thiodiglycolate and 0.1 g. of orthophosphoric acid, there is dissolved 3.80 g. of penicillin V sulfoxide methyl ester and the resulting solution is reacted and after-treated in the same manner as Example 2. The procedure yields 2.35 g. (64.9%) of 7-phenoxyacetamido-3-desacetoxycephalosporanic acid methyl ester.

EXAMPLE 21

(1) In 200 ml. of dioxane is dissolved 4.56 g. of penicillin G sulfoxide $\beta$-methylsulfonylethyl ester and 0.196 g. of orthophosphoric acid and the mixture is refluxed under nitrogen streams for 18 hours, wherein the condensed vapor is guided through a cylinder of filter paper packed with barium oxide before it is returned to the reactor to remove the water. The reaction mixture thus obtained is cooled and the dioxane is distilled off under reduced pressure. The residue is dissolved in 200 ml. of methylene chloride and the solution is washed with 1% aqueous sodium hydrogen carbonate and water in that order. The solution is dried and the methylene chloride is distilled off under reduced pressure to give an oily residue, which is subjected to the column-chromatography packed with silica-gel and eluted with methylene chloride-ethyl acetate(1:3). From the eluate, 2.10 g. (45.9%) of 7-phenylacetamido-3-desacetoxycephalosporanic acid $\beta$-methylsulfonylethyl ester is obtained.

(2) Using 45.6 g. of penicillin G sulfoxide $\beta$-methylsulfonylethyl ester, 1.77 g. of pyridinium phosphate and 1 liter of dioxane, the procedure as above (1) is repeated to obtain 32.8 g. (74.8%) of 7-phenylacetamido-3-desacetoxycephalosporanic acid $\beta$-methylsulfonylethyl ester.

(3) Using 45.6 g. of penicillin G sulfoxide $\beta$-methylsulfonylethyl ester, 6.35 g. of di-n-propyl sulfide, 0.98 g. of orthophosphoric acid and 1 liter of dioxane, the above procedure as above (1) is repeated to obtain 37.4 g. (85.4%) of 7-phenylacetamido-3-desacetoxycephalosporanic acid $\beta$-methylsulfonylethyl ester.

EXAMPLE 22

In 50 ml. of dioxane containing 0.96 g. of $\gamma$-hydroxypropylethyl sulfide and 0.19 g. of orthophosphoric acid, there is dissolved 4.56 g. of penicillin G sulfoxide $\beta$-methylsulfonylethyl ester and the resulting solution is refluxed. In nitrogen gas streams, the reaction is conducted for 14 hours while the water is removed from the reflux circuit with calcium oxide. After the reaction has been completed, the dioxane is distilled off under reduced pressure and the residue is dissolved in 100 ml. of methylene chloride, followed by washing with 1% sodium hydrogen carbonate and, then, with sodium chloride (50 ml. each). The solution is dried and the methylene chloride is distilled off under reduced pressure, whereupon yellow crystals are obtained. These crystals are recrystallized from acetone-petroleum ether. The mother fluid is treated in the same manner as Example 14. The procedure yields 3.64 g. (83.1%) of 7-phenylacetamido-3-desacetoxycephalosporanic acid $\beta$-methylsulfonylethyl ester.

EXAMPLE 23

In 50 ml. of a mixture (3:1) of sec.-butanol and chlorobenzene containing 0.96 g. of $\gamma$-hydroxypropyl ethyl sulfide and 0.23 g. of orthophosphoric acid, there is dissolved 4.56 g. of penicillin G sulfoxide $\beta$-methylsulfonylethyl ester, followed by refluxing (b.p.105° C.). The reaction is carried out and the reaction product is after-treated in the same manner as Example 22. The procedure yields 3.06 g. (69.9%) of 7-phenylacetamido-3-desacetoxycephalosporanic acid $\beta$-methylsulfonylethyl ester.

EXAMPLE 24

In 50 ml. of dioxane containing 0.84 g. of $\gamma\gamma'$-dihydroxypropyl sulfide and 0.16 g. of orthophosphoric acid, there is dissolved 4.56 g. of penicillin G sulfoxide $\beta$-methylsulfonylethyl ester and the solution is refluxed. The reaction is conducted for 16 hours and the reaction mixture is after-treated in the same manner as Example 22. The procedure yields 3.72 g. (84.9%) of 7-phenylacetamido-3-desacetoxycephalosporanic acid $\beta$-methylsulfonylethyl ester.

EXAMPLE 25

(1) In 110 ml. of a mixture (7:4) of 1,1,2,2-tetrachlorethane and tert.-butanol, are dissolved 4.56 g. of penicillin G sulfoxide $\beta$-methylsulfonylethyl ester, 0.90 g. of di-n-propyl sulfide and 0.16 g. of orthophosphoric acid. The solution is heated under reflux (internal temperature 106° C.). The condensed vapor is guided through a dryer (calcium oxide, molecular-cieve, etc.) before it is returned to the reactor to remove the water. The reaction system is held under reflux in nitrogen gas streams for 12 hours. After the reaction has been completed, the solvent is distilled off under reduced pressure. The residue is dissolved in 100 ml. of methylene chloride and the solution is washed with 1% aqueous sodium hydrogen carbonate and aqueous sodium chloride in that order. The solution is dried and the methylene chloride is distilled off under reduced pressure, whereupon a yellowish solid residue is obtained. This solid is recrystallized from acetone-petroleum ether. The mother fluid is concentrated and column-chromatographed on silica gel. The procedure yields 3.69 g. (yield 84.2%) of 7-phenylacetamido-3-desacetoxycephalosporanic acid $\beta$-methylsulfonylethyl ester.

(2) The same procedure above (1) except not employing di-n-propyl sulfide is repeated to give 1.76 g. (40.2%) of 7-phenylacetamido-3-deacetoxycephalosporanic acid $\beta$-methylsulfonylethyl ester.

(3) Employing 0.29 g. of pyridinium phosphate instead of 0.90 g. of di-n-propyl sulfide and 0.16 of orthophosphate, the above procedure (1) is repeated to give 2.88 g. (65.7%) of 7-phenylacetamido-3-deacetoxycephalosporanic acid β-methylsulfonylethyl ester.

EXAMPLE 26

In 100 ml. of a mixture (7:4) of 1,1,2,2-tetrachloroethane and tert.-butanol, are heated under reflux a mixture of 4.72 g. of penicillin V sulfoxide β-methylsulfonylethyl ester, 0.85 g. of 1,4-dithiane and 0.20 g. of methanesulfonic acid. The solution is reacted for 15 hours and the reaction mixture is after-treated in the same manner as Example 25 (1). The procedure yields 2.92 g. (64.3%) of 7-phenoxyacetamido-3-desacetoxycephalosporanic acid β-methylsulfonylethyl ester.

EXAMPLE 27

In 120 ml. of a mixture (1:1) of 1,1,2,2-tetrachlorethane and tert.-amyl alcohol, are dissolved 4.56 g. of penicillin G sulfoxide β-methylsulfonylethyl ester, 1.0 g. of di-n-propyl sulfide and 0.18 g. of orthophosphoric acid and the solution is refluxed (internal temperature 118° C.). The reaction is conducted for 4 hours and the reaction mixture is after-treated in the same manner as Example 25(1). The procedure yields 3.80 g. (86.7%) of 7-phenylacetamido-3-desacetoxycephalosporanic acid β-methylsulfonylethyl ester.

EXAMPLE 28

In 100 ml. of a mixture (1:1) of 1,1,2,2-tetrachlorethane and tert.-amyl alcohol, are dissolved 4.56 g. of penicillin G sulfoxide β-methylsulfonylethyl ester, 0.45 g. of silica phosphate (powder of P/Si=1 containing 50% water) and 0.75 g. of pentamethylene sulfide and the solution is refluxed. The reaction is conducted for 5 hours in the same manner as Example 25(1). After the reaction has been completed, the mixture is filtrated with the aid of Hyflo Super-cel. The filtrate is concentrated under reduced pressure and the residue is treated in the same manner as Example 25(1). The procedure yields 3.68 g. (84.0%) of 7-phenylacetamido-3-desacetoxycephalosporanic acid β-methylsulfonylethyl ester.

EXAMPLE 29

In 1.2 liter of a mixture (1:1) of 1,1,2,2-tetrachlorethane and tert.-amyl alcohol, are dissolved 45.6 g. of penicillin G sulfoxide β-methylsulfonylethyl ester, 10.5 g. of di-n-propyl sulfide and 1.70 g. of orthophosphoric acid and the solution is refluxed. The reaction is conducted for 5 hours and the reaction mixture is after-treated in the same manner as Example 25(1). The procedure yields 38.3 g. (87.4%) of 7-phenylacetamido-3-desacetoxycephalosphoric acid β-methylsulfonylethyl ester.

EXAMPLE 30

In 100 ml. of a mixture (7:3) of 1,1,2,2-tetrachlorethane and isopropyl alcohol, there are dissolved 4.56 g. of penicillin G sulfoxide β-methylsulfonylethyl ester, 0.95 g. of di-n-propyl sulfide and 0.18 g. of orthophosphoric acid and the solution is refluxed (internal temperature 107° C.). The reaction is conducted for 12 hours and the reaction mixture is after-treated in the same manner as Example 25(1). The procedure yields 3.14 g. (71.1%) of 7-phenylacetamido-3-desacetoxycephalosporanic acid β-methylsulfonylethyl ester.

EXAMPLE 31

In 100 ml. of a mixture (7:3) of 1,1,2,2-tetrachlorethane and sec.-butanol, there are dissolved 4.56 g. of penicillin G sulfoxide β-methylsulfonylethyl ester, 1.20 g. of diethyl thiodiglycolate and 0.18 of orthophosphoric acid and the solution is refluxed (internal temperature 115° C.). The reaction is conducted for 6 hours and the reaction mixture is after-treated in the same manner as Example 25(1). The procedure yields 2.94 g. (67.2%) of 7-phenylacetamido-3-desacetoxycephalosphoranic acid β-methylsulfonylethyl ester.

EXAMPLE 32

In 120 ml. of a mixture (1:1) of 1,1,1,2-tetrachlorethane and tert.-amyl alcohol, there are dissolved 6.22 g. of 6-(D-N-(β-methylsulfonylethoxycarbonyl)-phenylglycylamido) penicillanic acid-1-oxide β-methylsulfonylethyl ester, 0.83 g. of n-propyl ethyl sulfide and 0.16 g. of orthophosphoric acid and the solution is refluxed.

The reaction is conducted for 8 hours and treated in the same manner as Example 25(1). The resulting solution is subjected to chromatography using a silica gel column and eluted with a mixture of methylene chloride and ethyl acetate (1:3). The procedure yields 4.35 g. (72.1%) of 7-(D-N-(β-methylsulfonylethoxycarbonyl)-phenylglycylamido)-3-desacetoxycephalosporanic acid β-methylsulfonylethyl ester.

IR(KBr disc): 1778, 1727, 1695, 1665, 1535cm$^{-1}$.

NMR (d$_6$-DMSO): δ2.04(3H), 2.97(6H), 3.40(6H), 4.42(4H), 5.13(1H), 5.46(2H), 7.30(5H), 7.95(1H), 9.16(1H) ppm.

EXAMPLE 33

In 110 ml. of a mixture (7:3) of 1,1,1,2-tetrachlorethane and tert.-butanol, there are dissolved 4.06 g. of penicillin G sulfoxide tert.-butyl ester, 1.10 g. of di-n-butyl sulfide and 0.16 g. of orthophosphoric acid and the solution is refluxed. The reaction is conducted for 16 hours and the reaction mixture is treated in the same manner as Example 25(1). The procedure yields 2.99 g. (79.2%) of 7-phenylacetamido-3-desacetoxycephalosporanic acid tert.-butyl ester. m.p.139°–144° C.

IR(KBr disc): 3300, 1770, 1713, 1658, 1540cm$^{-1}$.

NMR(CDCl$_3$): δ1.50(9H), 2.08(3H), 3.30(2H), 3.80(2H), 4.89(1H), 5.76(1H), 7.10(1H), 7.27(5H) ppm.

EXAMPLE 34

In 120 ml. of a mixture (1:1) of 1,1,2-trichloroethane and tert.-amyl alcohol, there are dissolved 4.56 g. of penicillin G sulfoxide β-methylsulfonylethyl ester, 1.0 g. of di-n-propyl sulfide and 0.18 g. of orthophosphoric acid and the solution is refluxed (internal temperature 105° C.). The reaction is conducted for 13 hours in the same manner as Example 25(1). The procedure yields 3.53 g. (80.6%) of 7-phenylacetamido-3-desacetoxycephalosporanic acid β-methylsulfonylethyl ester.

EXAMPLE 35

In 120 ml. of a mixture (1:1) of 1,1,2-trichlorethane and tert-amyl alcohol, there are dissolved 4.98 g. of penicillin V sulfoxide β,β,β-trichlorethyl ester, 1.15 g. of dibenzyl sulfide and 0.38 g. of D-camphor-10-sulfonic acid and the solution is refluxed. The reaction is conducted for 13 hours in the same manner as Example 25(1). After the reaction has been completed, the solvent is distilled off under reduced pressure. The residue is dissolved in methylene chloride and the solution is washed with 1% aqueous sodium hydrogen carbonate and water in that order. The solution is dried and the methylene chloride is distilled off. The residue is subjected to chromatography using silica gel column and eluted with a mixture of methylene chloride and ether (1:1). The procedure yields 2.94 g. of 7-phenoxyacetamido-3-desacetoxycephalosporanic acid β,β,β-trichlorethyl ester. m.p.114°–116° C.

IR(KBr disc): 1786, 1742, 1690cm$^{-1}$.

NMR(CDCl$_3$): δ2.19(3H), 3.37(2H), 4.56(2H), 4.8–5.2(3H), 5.83(1H), 6.8–7.6(6H) ppm.

EXAMPLE 36

In 110 ml. of a mixture (7:4) of 1,1,2-trichloroethane and 3-pentanol, there are dissolved 4.56 g. of penicillin G sulfoxide β-methylsulfonylethyl ester, 0.90 g. of di-n-propyl sulfide and 0.17 g. of orthophosphoric acid and the solution is refluxed (internal temperature 112° C.). The reaction is conducted for 8 hours and the reaction mixture is treated in the same manner as Example 25(1). The procedure yields 3.38 g. (77.2%) of 7-phenylacetamido-3-desacetoxycephalosporanic acid β-methylsulfonylethyl ester.

EXAMPLE 37

In 100 ml. of a mixture (7:3) of 1,1,2-trichloroethane and sec.-butanol, there are dissolved 4.56 g. of penicillin G sulfoxide β-methylsulfonylethyl ester, 1.0 g. of di-n-propyl sulfide and 0.19 g. of orthophosphoric acid and the solution is refluxed (internal temperature 105° C.). The reaction is conducted for 3 hours and the reaction mixture is treated in the same manner as Example 25(1). The procedure yields 2.77 g. (63.2%) of 7-phenylacetamido-3-desacetoxycephalosporanic acid β-methylsulfonylethyl ester.

EXAMPLE 38

In 140 ml. of a mixture (4:3) of 1,2-dichloropropane and tert.-amyl alcohol, there are dissolved 4.56 g. of penicillin G sulfoxide β-methylsulfonylethyl ester, 0.95 g. of di-n-propyl sulfide and 0.20 g. of orthophosphoric acid and the solution is refluxed (internal temperature 98° C.). The reaction is conducted for 19 hours and the reaction mixture is after-treated in the same manner as Example 25(1). The procedure yields 3.30 g. (72.9%) of 7-phenylacetamido-3-desacetoxycephalosporanic acid β-methylsulfonylethyl ester.

EXAMPLE 39

In 100 ml. of a mixture (7:3) of 1,2-dichloropropane and 3-pentanol, there are dissolved 4.56 g. of penicillin G sulfoxide β-methylsulfonylethyl ester, 1.0 g. of di-n-propyl sulfide and 0.18 g. of orthophosphoric acid and the solution is refluxed (internal temperature 100° C.). The reaction is conducted for 15 hours and the reaction mixture is after-treated in the same manner as Example 25(1). The procedure yields 2.57 g. (58.6%) of 7-phenylacetamido-3-desacetoxycephalosporanic acid β-methylsulfonylethyl ester.

EXAMPLE 40

In 110 ml. of a mixture (7:4) of 1,2-dichloropropane and sec.-amyl alcohol, there are dissolved 4.56 g. of penicillin G sulfoxide β-methylsulfonylethyl ester, 1.10 g. of di-tert.-butyl sulfide and 0.18 g. of orthophosphoric acid and the solution is refluxed (internal temperature 103° C.). The reaction is conducted for 11 hours and the reaction mixture is after-treated in the same manner as Example 25(1). The procedure yields 2.71 g. (61.8%) of 7-phenylacetamido-3-desacetoxycephalosporanic acid β-methylsulfonylethyl ester.

EXAMPLE 41

(1) In 140 ml. of tert.-amyl alcohol, there are dissolved 4.56 g. of penicillin G sulfoxide β-methylsulfonylethyl ester, 1.10 g. di-n-propyl sulfide and 0.20 g. of orthophosphoric acid and the solution is refluxed. The reaction is conducted for 15 hours and the reaction mixture is after treated in the same manner as Example 25(1). The procedure yields 3.32 g. (75.8%) of 7-phenylacetamido-3-desacetoxycephalosporanic acid β-methylsulfonylethyl ester.

(2) The above procedure is repeated without employing di-n-propyl sulfide to give 1.64 g. (37.5%) of the objective compound.

EXAMPLE 42

In 100 ml. of tert.-amyl alcohol, there are dissolved 4.16 g. of 6-(α-chloroacetamido)-pencillanic acid-1-oxide β-methylsulfonylethyl ester, 0.85 g. of ethyl n-propyl sulfide and 0.16 g. of orthophosphoric acid and the solution is refluxed. The reaction is conducted for 15 hours in the same manner as Example 25(1) and the reaction mixture is after-treated by a procedure similar to that described in Example 35. The procedure yields 2.79 g. (70.2%) of 7-(α-chloroacetamido)-3-desacetoxycephalosporanic acid β-methylsulfonylethyl ester.

EXAMPLE 43

In 200 ml. of a mixture (3:2) of methyl N,N'-dimethylcarbamate ester and benzene, there are dissolved 9.12 g. of penicillin G sulfoxide β-methylsulfonylethyl ester, 1.80 g. of di-n-propyl sulfide and 0.32 g. of orthophosphoric acid and the solution is refluxed (internal temperature 105° C.). The reaction is conducted for 10 hours and the reaction mixture is after-treated in the same manner as Example 25(1). The procedure yields 7.05 g. (80.6%) of 7-phenylacetamido-3-desacetoxycephalosporanic acid β-methylsulfonylethyl ester.

EXAMPLE 44

In 240 ml. of a mixture (1:1) of methyl N,N'-dimethylcarbamate and tert.-butanol, there are dissolved 9.12 g. of penicillin G sulfoxide β-methylsulfonylethyl ester, 1.80 g. of di-n-propyl sulfide and 0.32 g. of orthophosphoric acid and the solution is refluxed (internal temperature 101° C.). The reaction is conducted for 11 hours in the same manner as Example 25(1). The procedure yields 7.19 g. (82.1%) of 7-phenylacetamido-3-desacetoxycephalosporanic acid β-methylsulfonylethyl ester.

EXAMPLE 45

In a mixture (1:1) of methyl N,N'-dimethylcarbamate and tert.-amyl alcohol, there are dissolved 4.56 g. of penicillin G sulfoxide β-methylsulfonylethyl ester, 1.0 g. of di-n-propyl sulfide and 0.18 g. of orthophosphoric acid and the solution is refluxed (internal temperature 117° C.).

The reaction is conducted for 4 hours and the reaction mixture is after-treated in the same manner as Example 25(1). The procedure yields 3.56 g. (81.3%) of 7-phenylacetamido-3-desacetoxycephalosporanic acid β-methylsulfonylethyl ester.

EXAMPLE 46

In 100 ml. of a mixture (3:2) of ethyl N,N'-dimethylcarbamate and benzene, there are dissolved 4.56 g. of penicillin G sulfoxide β-methylsulfonylethyl ester, 0.85 g. of ethyl n-propyl sulfide and 0.19 g. of orthophosphoric acid and the solution is refluxed. The reaction is conducted for 8 hours and the reaction mixture is after-treated in the same manner as Example 25(1). The procedure yields 3.38 g. (77.2%) of 7-phenylacetamido-3-desacetoxycephalosporanic acid β-methylsulfonylethyl ester.

EXAMPLE 47

In 120 ml. of a mixture (1:1) of n-butyl acetate and tert.-amyl alcohol, there are dissolved 4.56 g. of penicillin G sulfoxide β-methylsulfonylethyl ester, 0.90 g. of di-n-propyl sulfide and 0.17 g. of orthophosphoric acid and the solution is refluxed (internal temperature 110° C.). In the same manner as Example 25(1), the reaction is conducted for 11 hours and the reaction mixture is after-treated. The procedure yields 3.62 g. (82.6%) of 7-phenylacetamido-3-desacetoxycephalosporanic acid β-methylsulfonylethyl ester.

EXAMPLE 48

In 100 ml. of a mixture (1:1) of ethyl N,N'-dimethylcarbamate and tert.-butanol, there are dissolved 4.56 g. of penicillin G sulfoxide β-methylsulfonylethyl ester, 1.05 g. of di-n-butyl sulfide and 0.17 g. of orthophosphoric acid and the solution is refluxed. In the same manner as Example 25(1), the reaction is conducted for 8 hours to obtain 3.51 g. (80.1%) of 7-phenylacetamido-3-desacetoxycephalosporanic acid β-methylsulfonylethyl ester.

EXAMPLE 49

In 140 ml. of tert.-amyl alcohol, there are dissolved 4.72 g. of penicillin V sulfoxide β-methylsulfonylethyl ester, 1.10 g. of di-tert.-butyl sulfide and 0.18 g. of orthophosphoric acid and the solution is refluxed. In the same manner as Example 25(1), the reaction is conducted for 15 hours and the reaction mixture is after-treated. The procedure yields 3.47 g. (76.2%) of 7-phenylacetamido-3-desacetoxycephalosporanic acid β-methylsulfonylethyl ester.

EXAMPLE 50

In 100 ml. of a mixture (2:2:1) of 1,2-dichloroethane, sec.-amyl alcohol and toluene, there are dissolved 4.56 g. of penicillin G sulfoxide β-methylsulfonylethyl ester, 0.90 g. of di-n-propyl sulfide and 0.18 g. of orthophosphoric acid and the solution is refluxed (internal temperature 101° C.). In the same manner as Example 25(1), the reaction is conducted for 16 hours and the reaction mixture is after-treated. The procedure yields 2.81 g. (64.1%) of 7-phenylacetamido-3-desacetoxycephalosporanic acid β-methylsulfonylethyl ester.

EXAMPLE 51

(1) The procedure described in Example 21(1) is repeated except employing 3.80 g. of penicillin V sulfoxide methyl ester in place of 4.56 g. of penicillin G sulfoxide β-methylsulfonylethyl ester to give 1.66 g. (46%) of 7-phenoxyacetamido-3-desacetoxycephalosporanic acid methyl ester.

(2) The procedure described in Example 21(2) is repeated except employing 38.0 g. of penicillin V sulfoxide methyl ester in place of 45.6 g. of penicillin G sulfoxide β-methylsulfonylethyl ester to give 26.4 g. (73%) of 7-phenoxyacetamido-3-desacetoxycephalosporanic acid methyl ester.

(3) The procedure described in Example 21(3) is repeated except employing 38.0 g. of penicillin V sulfoxide methyl ester in place of 45.6 g. of pencillin G sulfoxide β-methylsulfonylethyl ester to give 30.4 g. (85%) of 7-phenoxyacetamido-3-desacetoxycephalosporanic acid methyl ester.

What we claim is:

1. In a process for producing a 3-desacetoxycephalosporin of the formula

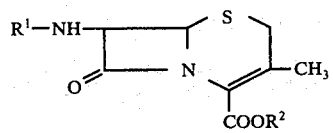

wherein $R^1$ represents a protective group for the amino group and $R^2$ represents hydrogen or a protective group for the carboxyl group, by heating a penicillin-1-oxide of the formula

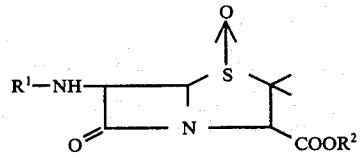

wherein $R^1$ and $R^2$ have the same meanings as above, in the presence of an acid catalyst selected from the group consisting of phosphoric acid, orthophosphoric acid, polyphosphoric acid, pyrophosphoric acid, methanephosphonic acid, ethanephosphonic acid, trichloromethanesphosphonic acid, iodomethanephosphonic acid, benzenephosphonic acid, bromobenzenephosphonic acid, nitrobenzenephosphonic acid, β-iodoethyl phosphate, β-bromoethyl phosphate, β-methoxyethyl phosphate, β,β,β-trichloroethyl phosphate, 2-chloroethyl phosphate, benzyl phosphate, p-tolyl phosphate, methyl phosphate, ethyl phosphate, phenyl phosphate, 1-naphthyl phosphate, 2-naphthyl phosphate, 10-D-camphorsulfonic acid, methanesulfonic acid, p-toluenesulfonic acid, silicaalumina, silica-boria, silica-magnesia, silica-zirconia, aluminaboria, thoria-silica, thoria-alumina, silica-alumina-zirconia, silica-alumina-magnesia, silica-alumina-thoria, natural zeolite, acid clay, kaolin, bentonite and silica phosphate, in an inert organic solvent, the improvement wherein the heating is carried out in the presence of an organic sulfide, having a molecular weight of up to 500, selected from the group consisting of diethyl sulfide, ethyl n-propyl sulfide, ethyl isopropyl sulfide, di-n-propyl sulfide, di-n-butyl sulfide, n-butyl ethyl sulfide, dodecyl methyl sulfide, di-tert-butyl sulfide, 1,2-di(methylmercapto)ethane, 1,2-di(n-dodecylmercapto)ethane, tetramethylene sulfide, pentamethylene sulfide, 1,4-dithiane, s-trithiane, phenylmethyl sulfide, 2-thienylethyl sulfide, diphenyl sulfide, dibenzyl sulfide, β-hydroxyethylmethyl sulfide, γ-hydroxypropylethyl sulfide, thiodiglycol, γ,γ'-dihydroxypropyl sulfide, 1,2-di(2-hydroxyethylthio)ethane, δ-hydroxypentylethyl sulfide, 2-hydroxypropylethyl sulfide, β,β'-diethoxyethyl sulfide, ethylethoxymethyl sulfide, β-hydroxyethylphenyl sulfide, β-ethylmercaptoethyl methyl ketone, dimethyl thiodiglycollate, diethyl thiodiglycollate, 2,2'-dicyanoethyl sulfide and polypropylene sulfide.

2. A process to claim 1, wherein the protective group for the amino group is an acyl group.

3. A process according to claim 1, wherein the organic sulfide is selected from the group consisting of diethyl sulfide, ethyl n-propyl sulfide, ethyl isopropyl sulfide, di-n-propyl sulfide, di-n-butyl sulfide, n-butyl ethyl sulfide, dodecyl methyl sulfide and di-tert-butyl sulfide.

4. The process of claim 1, wherein said acid catalyst is selected from the group consisting of orthophosphoric acid, pyrophosphoric acid and polyphosphoric acid.

5. The process of claim 1, wherein said acid catalyst is selected from the group consisting of

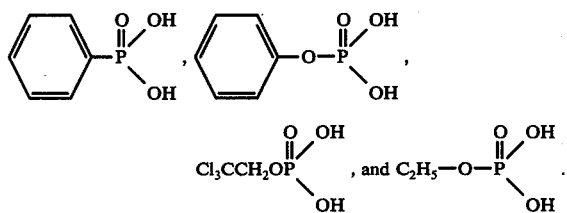

6. A process according to claim 3 wherein the sulfide is diethyl sulfide.

7. A process according to claim 3, wherein the sulfide is ethyl n-propyl sulfide.

8. A process according to claim 3, wherein the sulfide is ethyl isopropyl sulfide.

9. A process according to claim 1, wherein the organic sulfide is 1,2-di(methylmercapto)ethane.

10. A process according to claim 3, wherein the sulfide is di-n-propylsulfide.

11. A process according to claim 3, wherein the sulfide is di-tert.-butyl sulfide.

12. A process according to claim 3, wherein the sulfide is di-n-butyl sulfide.

13. The process of claim 1, wherein said acid catalyst is 4-toluenesulfonic acid.

14. A process according to claim 1, wherein the organic sulfide is pentamethylene sulfide.

15. A process according to claim 1, wherein the organic sulfide is 1,4-dithiane.

16. A process according to claim 1, wherein the organic sulfide is s-trithiane.

17. The process of claim 1, wherein said penicillin-1-oxide is heated to from 80° to 150° C. in the presence of said catalyst.

18. A process according to claim 1, wherein the organic sulfide is phenylmethyl sulfide.

19. A process according to claim 1, wherein the organic sulfide is diphenyl sulfide.

20. A process according to claim 1, wherein the organic sulfide is dibenzyl sulfide.

21. A process according to claim 1, wherein the organic sulfide is 2-thienylethyl sulfide.

22. The process of claim 1, wherein said catalyst is an inorganic phosphoric acid and said organic sulfide is diethylsulfide.

23. A process according to claim 1, wherein the organic sulfide is β-hydroxyethyl methyl sulfide.

24. A process according to claim 1, wherein the organic sulfide is γ-hydroxypropyl ethyl sulfide.

25. A process according to claim 1, wherein the organic sulfide is β-hydroxyethylphenyl sulfide.

26. A process according to claim 1, wherein the organic sulfide is thiodiglycol.

27. A process according to claim 1, wherein the organic sulfide is 2,2'-dicyanoethylsulfide.

28. A process according to claim 1, wherein the organic sulfide is γ,γ'-dihydroxypropyl sulfide.

29. A process according to claim 1, wherein the organic sulfide is 2-hydroxypropyl ethyl sulfide.

30. The process of claim 4, wherein said sulfide is $C_2H_5$-S-$C_2H_5$, $(CH_3)_2$-CH-S-$C_2H_5$, $C_3H_7$-S-$C_3H_7$, $C_4H_9$-S-$C_4H_9$, or $(CN\ CH_2\ CH_2)_2S$.

31. A process according to claim 1, wherein the organic sulfide is β,β'-diethoxyethyl sulfide.

32. A process according to claim 1, wherein the organic sulfide is ethyl ethoxymethyl sulfide.

33. A process according to claim 1, wherein the organic sulfide is β-ethylmercaptoethyl methyl ketone.

34. A process according to claim 1, wherein the organic sulfide is dimethyl thiodiglycollate.

35. A process according to claim 1, wherein the organic sulfide is diethyl thiodiglycollate.

* * * * *